United States Patent [19]
Rutten

[11] Patent Number: 6,148,238
[45] Date of Patent: Nov. 14, 2000

[54] PACING LEADS HAVING A BRACHIOCEPHALIC TINE OR STAR TINE

[75] Inventor: Jean J. G. Rutten, El Bocholtz, Netherlands

[73] Assignee: Medtronic, Inc., Minneapolis, Minn.

[21] Appl. No.: 09/131,904

[22] Filed: Aug. 10, 1998

[51] Int. Cl.[7] ......................................................... A61N 1/05
[52] U.S. Cl. ........................................................... 607/126
[58] Field of Search .................................... 607/122, 123, 607/128, 126

[56] References Cited

U.S. PATENT DOCUMENTS

| | | | |
|---|---|---|---|
| 3,865,118 | 2/1975 | Bures | 128/404 |
| 4,154,247 | 5/1979 | O'Neill | 128/418 |
| 4,386,615 | 6/1983 | Sowton | 128/786 |
| 5,190,052 | 3/1993 | Schroeppel | 128/786 |
| 5,300,107 | 4/1994 | Stokes et al. | 607/126 |
| 5,324,327 | 6/1994 | Cohen | 607/122 |
| 5,628,778 | 5/1997 | Kruse et al. | 607/123 |

OTHER PUBLICATIONS

Brownlee, Robert R. et al., "Toward Optimizing a Preshaped Catheter and System Parameters to Achieve Single Lead DDD Pacing," *PACE*, vol. 20, May 1997, Part I, pp. 1354–1358.

*Primary Examiner*—Scott M. Getzow
*Attorney, Agent, or Firm*—Thomas F. Woods; Michael J. Jaro; Harold Patton

[57] ABSTRACT

The present invention provides a pacing system with a lead having a fixation element for providing stable fixation relative to the junction of the left and right brachiocephalic veins of the patient. In a first embodiment, a short tine element is provided for engaging the brachiocephalic junction. The present invention also provides a pacing system with a lead having a fixation element for providing stable fixation relative to the atrium and the SVC of the patient. In another embodiment, a three-pronged tine is provided for engaging the portion of the atrium adjacent the SVC.

15 Claims, 3 Drawing Sheets

PACING LEADS HAVING A BRACHIOCEPHALIC TINE OR STAR TINE

FIELD OF THE INVENTION

The present invention relates to the field of leads for pacing a heart, and more specifically, to leads which have an element for maintaining positioning of the lead within the atrium.

BACKGROUND OF THE INVENTION

It has long been a desire and aim in the pacemaker art to provide a reliable single lead for use with a dual chamber pacing system. As is known, in the past a conventional dual chamber system typically has utilized two leads which interconnect the implanted pacemaker with the ventricle and atrium, respectively. Thus, in such a system a ventricular lead interconnects the pacemaker with the ventricle, delivering ventricular pace pulses to the ventricle and sensing ventricular conduction activity and returning such sensed signals to the pacemaker. A second, atrial lead is provided for performing the same functions with respect to the atrium. A long recognized disadvantage of this arrangement is the need to provide two leads, which adds to expense and increases reliability problems; and also takes significantly more physician time in placing the two leads at time of implantation.

The VDD or VDD(R) single pass lead provides a response to the two-lead problem, and has been in use for some time. In such a single lead construction, the distal tip has a fixation mechanism for fixing to the apex of the ventricle, while the lead is essentially "floating" or unattached in the atrium. The VDD lead is provided with one or two atrial electrodes, typically ring electrodes which are positioned in the atrium, for sensing P wave signals, thereby providing the ability to time out an AV delay and provide ventricular pace pulses which are synchronized to sensed atrial depolarizations. While some attempts have been made to pace from floating atrial electrodes, this has generally been ineffectual.

A further advance is what is known as the DDD lead, which has enhancements which aim to provide more stable contact with the atrial wall, so as to enable more reliable atrial pacing as well as reliable atrial sensing. The DDD lead typically includes features added to the lead portion to enable DDD operation, i.e., pacing and sensing in both chambers. The additional features are intended to maintain the atrial electrodes closer to the atrial wall when the distal tip is anchored to the ventricular apex. These features may include, for example, an atrial tine, or small extension from the lead body, which may be designed to provide better fixation against the atrial wall. The atrial tine may also be provided with a distal electrode, for making direct contact with the atrial wall. Other features which have been adapted to DDD-type leads include a variety of S-shaped leads and pre-shaped sections, for the purpose of providing more stable atrial positioning. See, for example, U.S. Pat. No. 5,628,778, Kruse; and U.S. Pat. No. 4,154,247, O'Neill; and "Towards Optimizing a Pre-Shaped Catheter and System Parameters to Achieve Single Lead DDD Pacing," PACE, Vol.20, May 1997, Part I.

There remains, however, a significant need to improve the ability of the DDD lead to accommodate different heart sizes, as well as heart movement due to ongoing contractions.

Existing DDD leads are, to various degrees, not stable in the atrial area, do not adapt to heart size, and cannot move optimally with the heart during cardiac movement. There remains a significant need to adapt the DDD lead to heart movement and size, and to provide better anchoring with respect to the atrium.

SUMMARY OF THE INVENTION

In accordance with the above, the present invention is directed to a cardiac pacing system which incorporates a pacing lead having an element for substantially fixing a portion of the lead with respect to the junction of the patient's right and left brachiocephalic veins. The pacing lead of the present invention has a distal end and a proximal end, and a lead body extending therebetween. The lead further has a ventricular electrode which is positioned at about the distal end of the lead, and a ventricular conductor extending within the lead body through a lumen from the proximal end of the lead to the ventricular electrode. The pacing lead also has an element for substantially fixing a portion of the lead with respect to the junction of the left and right brachiocephalic veins when the distal end of the lead is at about the patient's ventricular apex and the lead is positioned to extend proximally from the junction through a portion of the patient's left brachycephalic vein. The fixation element suitably is a short tine element extending from the lead body at an angle corresponding to the angle of the junction formed by the left and right brachiocephalic veins.

The pacing lead also has an atrial lead body portion which is contiguous with and extends from the lead body and which has a distal end. An atrial electrode is positioned at about the distal end of the atrial lead body portion, and an atrial conductor extending within the atrial lead body portion through a lumen from the proximal end of the lead to the atrial electrode.

The present invention is also directed to a cardiac pacing system which incorporates a pacing lead having an element for substantially fixing a portion of the lead with respect to the junction of the atrium and the superior vena cava (SVC) when the distal end is at about the patient's ventricular apex and the lead is positioned to extend proximally from the junction of the atrium and the SVC through portion of the patient's left brachycephalic vein. The fixation element suitably is a three-pronged tine, which may optionally have an atrial electrode positioned at about the distal end of any or each of the three prongs. The three-pronged tine may also have an atrial conductor which extends through a lumen within any or each of the three prongs from the proximal end of the lead to the atrial electrodes.

DESCRIPTION OF THE PREFERRED EMBODIMENTS

Applicant's invention provides a pacing lead with a fixation element for providing stable fixation of the atrial electrodes near the sinus node. The fixation element may be positioned on the lead in order to substantially fix a portion of the lead with respect to the junction of the left and right brachiocephalic veins when the distal end of the lead is at about the patient's ventricular apex and the lead is positioned to extend proximally from the junction through a portion of the patient's left brachiocephalic vein. In addition, the fixation element may also be positioned on the lead in order to substantially fix a portion of the lead with respect to the junction of the atrium and the SVC when the distal end is at about the patient's ventricular apex and the lead is positioned to extend proximally from the junction through a portion of the patient's left brachiocephalic vein. Thus, as the heart contracts, the fixation element maintains positioning of the atrial portion of the lead.

Figure 1:
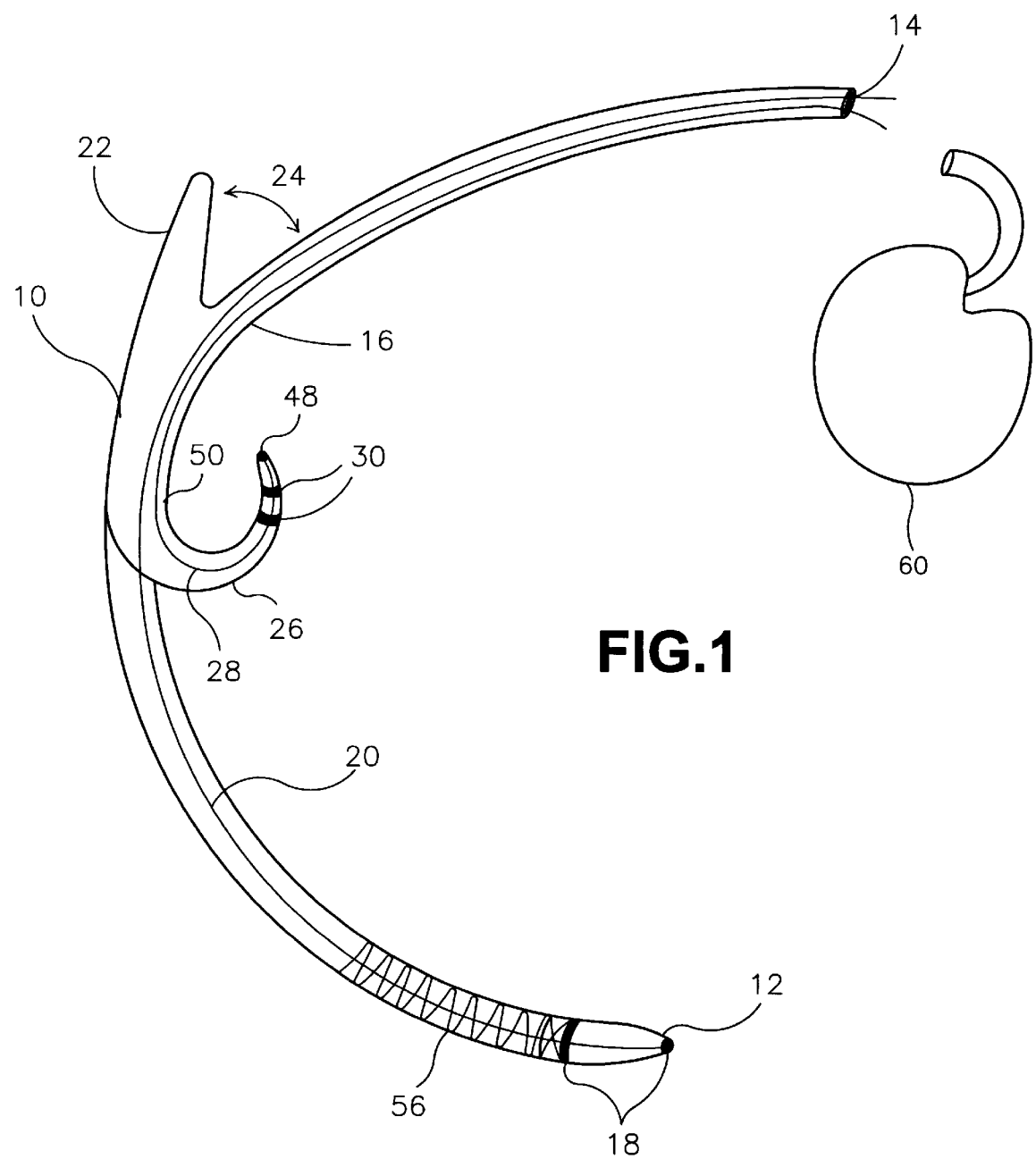
FIG. 1 is a diagrammatic sketch of a preferred system for pacing a patient's heart in which the lead has a fixation element for engaging the junction of the left and right brachiocephalic veins.
Figure 2:
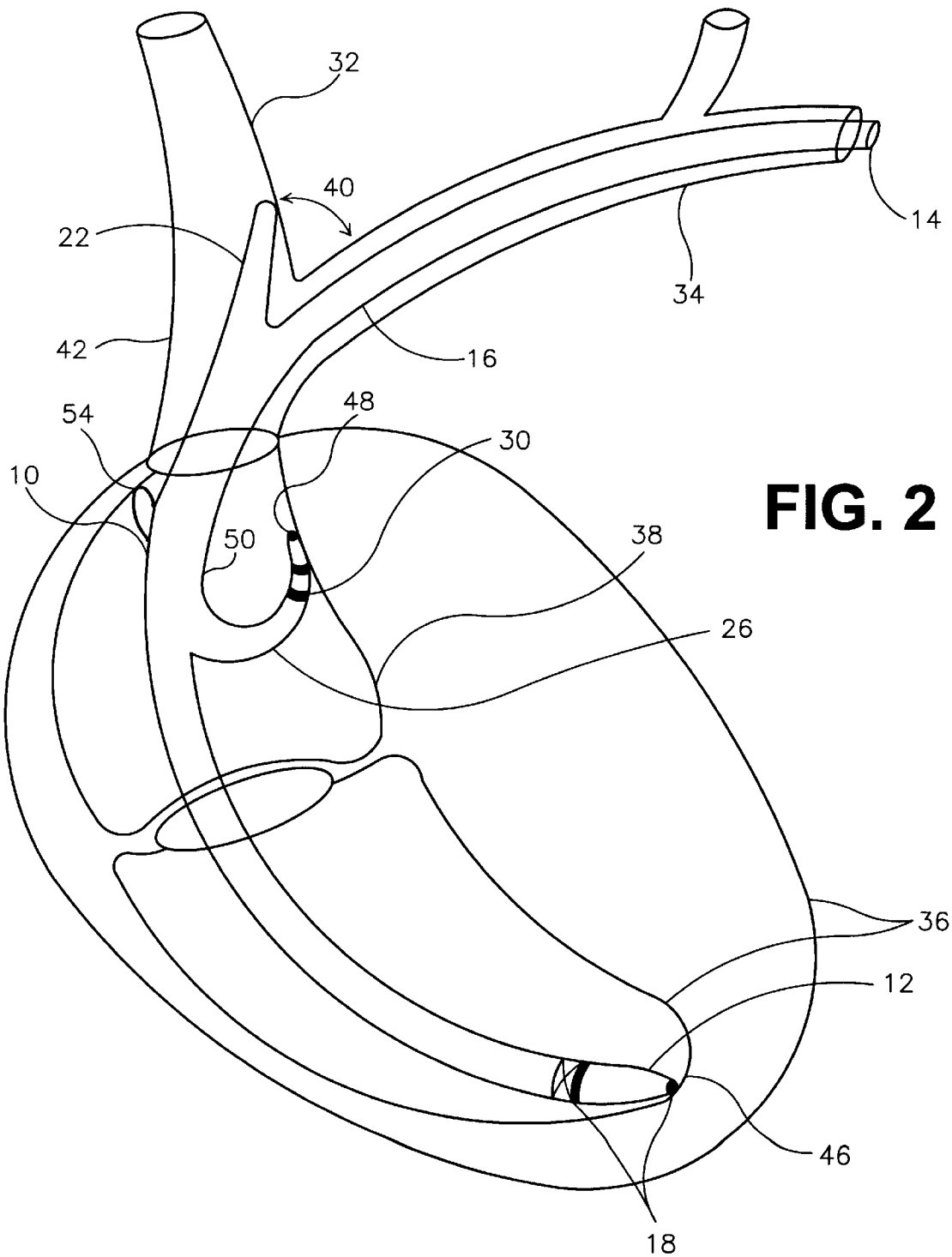
FIG. 2 is an illustrative representation of a first embodiment of a pacing lead in accordance with this invention, having a short tine element extending from the lead body at an angle corresponding to the angle of the junction of the left and right brachiocephalic veins.

Referring now to FIG. 1, there is shown an illustrative embodiment of a preferred pacing lead for pacing a patient's heart. The pacing lead 10 has a distal end 12 and a proximal end 14. The proximal end is connectable to a pacemaker 60. The distal end is positioned in the right ventricular apex 46 (as seen in FIG. 2) of the heart. A lead body 16 extends between the distal and proximal ends of the lead. The lead body is preferably made of non-conductive or insulative materials, such as silicone rubber, widely known to those skilled in the art of implantable leads. In addition, the lead body is preferably between about 1.0 and 4.0 mm in diameter, and more preferably between about 2.0 and 2.5 mm in diameter.

Still referring to FIG. 1, a preferred lead has a ventricular electrode 18 positioned at about the distal end of the lead and which engages the ventricle 36 (as seen in FIG. 2). The electrode is made of conductive materials well known those skilled in the art of leads. Preferably, the electrode is made of platina. The ventricular electrode may be a standard tip electrode known to those skilled in the art of leads or may be a ring electrode. Preferably, the ventricular electrode is positioned at about the distal end of the lead. A ventricular conductor 20 is within a lumen inside the lead body and connects the proximal end of the lead to the ventricular electrode. In preferred embodiments of the invention, the lead has two electrodes, e.g., one tip electrode and one ring electrode, or two ring electrodes. Of course, an embodiment of the invention contemplates a unipolar arrangement, using just one ventricular electrode, and using the pacemaker as the other reference electrode.

Still referring to FIG. 1, a preferred pacing lead has a curvilinear atrial lead body portion 26 which extends from the lead body and has a distal end 48. The atrial lead body portion is contiguous with the lead body of the lead and is preferably made of the same or similar material. At least one atrial electrode 30 is preferably positioned at about the distal end of the atrial lead body portion. The atrial electrode can be a standard tip electrode or a ring electrode as described above. The atrial lead body portion also has an atrial conductor 28 which extends within a lumen inside the atrial lead body portion from the atrial electrode to the proximal end of the lead. In preferred embodiments of the invention, the atrial electrode is a ring electrode. Although FIG. 2 shows the atrial lead body portion pointing towards the SVC 42, the atrial lead body portion may be positioned so as to point towards the ventricular apex.

Still referring to FIG. 1, a preferred lead also has a fixation element for fixing a portion of the lead with respect to the junction of the left 34 and right 32 brachiocephalic veins (as seen in FIG. 2) when the distal end of the lead is at about the patient's ventricular apex and the lead is positioned to extend proximally from the junction through a portion of the patient's left brachycephalic vein.

In a preferred embodiment of the invention, the fixation element is a short tine element 22 that limits the movement of the lead during heart contraction such that the atrial leads maintain engagement with the atrial wall 38 (as seen in FIG. 2). The short tine element extends from the lead body at an angle 24 substantially corresponding to the angle 40 (as seen in FIG. 2) of the junction between the right and left brachiocephalic veins. Angle 24 preferably is between about 45 and 60 degrees. Angle 24, however, can be made at any desired angle so as to correspond with angle 40 present in the heart. Preferably, the tine element is made of a flexible material and has an outer diameter of about 1.5 mm to about 2.0 mm. In addition, the tine element preferably is about 8 mm to about 12 mm in length, more preferably about 10 mm in length. The distance from the distal end of the lead to the short tine element is preferably from about 17 cm to about 25 cm. Preferably, the short tine element is positioned from about 7 cm to about 11 cm, more preferably 9 cm, proximal from the base 50 (as seen in FIG. 2) of the atrial lead body portion. In other embodiments of the invention, the lead may have a short tine element at the brachiocephalic junction as illustrated in FIG. 2 as well as a second atrial tine 54 positioned on the lead such that contact is facilitated between the second tine and the atrial wall when the ventricle is contracting.

In another embodiment of the present invention, the DDD pacing lead may be used in connection with tachycardia conditions, in addition to bradycardia conditions. Still referring to FIG. 1, the ventricular section of the DDD pacing lead may optionally comprise a ventricular defibrillation coil 56 connected to the ventricular ring electrode. The defibrillation coil is preferably between 3 and 10 cm long, most preferably 5 cm long. The defibrillation coil is preferably between about 2.5 and 3.0 mm in diameter, more preferably about 2.8 mm in diameter. The defibrillation coil is able to deliver a shock of about 34 joules. The tachycardia DDD lead is preferably connected to an implantable pacing cardioverter defibrillator, or any other type of arrhythmia management device known to those skilled in the art.

During testing of an embodiment of the invention having the brachiocephalic tine, the force imparted on the lead by the ventricular contractions did not result in the atrial section of the lead floating away from the atrial wall.

Indeed, as a result of the brachiocephalic tine, the atrial section of the lead was pushed against the atrial wall. In addition, a DDD lead with an atrial tine and a brachiocephalic tine was tested and achieved the same results. Thus, the brachiocephalic tine was able to maintain the location of the atrial section of the lead containing atrial electrodes, and even impart greater pressure on the atrial section of the lead against the atrial wall so as to maintain contact.

Figure 3A:
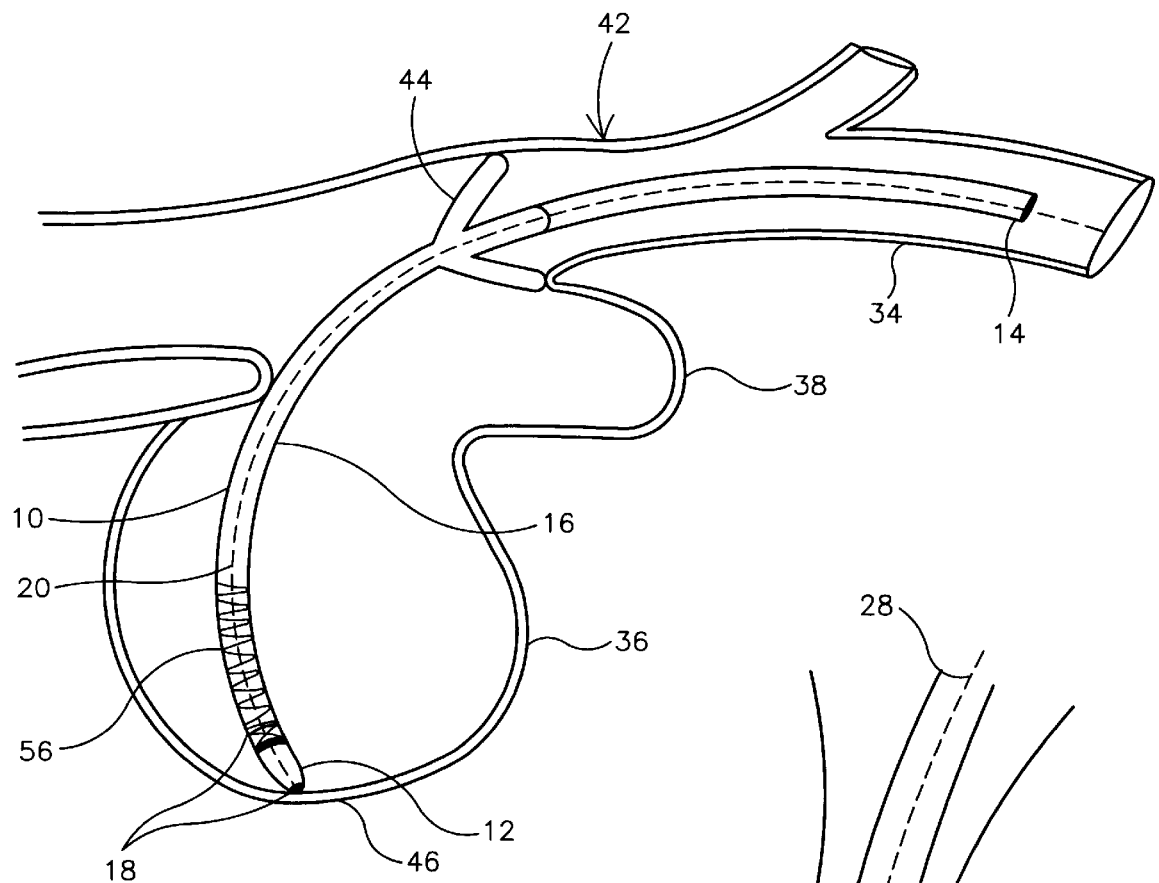
FIG. 3A is an illustrative representation of another embodiment of a pacing lead in accordance with this invention, having a three-pronged tine extending from the lead and positioned for fixation at the junction of the atrium and the SVC.
Figure 3B:
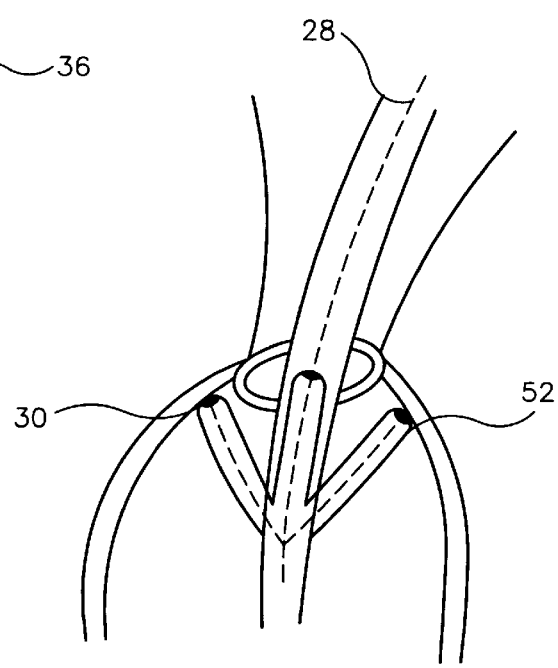
FIG. 3B is an illustrative representation of another embodiment of a three-pronged tine positioned for fixation at the junction of the atrium and the SVC, in which atrial electrodes are positioned at the distal ends of the three-pronged tine.

Referring now to FIG. 3, there is shown another preferred embodiment wherein the fixation element substantially fixes a portion of the lead with respect to the junction of atrium and the SVC when the distal end of the lead is at about the patient's ventricular apex and the lead is positioned to extend proximally from the junction of the atrium and the SVC through a portion of the patient's left brachycephalic vein. In a preferred embodiment of the invention, the fixation element is a three-pronged tine 44, also known as a "star" tine, which prevents the lead from shifting proximally through the atrium and into the SVC. The distance from the distal end of the lead to the three-pronged tine is preferably from about 10 cm to about 17 cm. Preferably, each prong of the tine is contiguous with the lead body attached thereto, and is made of a flexible material, such as, for example, silicone rubber. Each prong is preferably about 15 mm to about 20 mm in length and preferably has an outer diameter of about 1.5 mm to about 2.0 mm. An atrial electrode 30 is preferably positioned at about the distal end 52 of any or each of the three prongs, and an atrial conductor 28 extends within a lumen in any or each of the three prongs from the atrial electrodes to the proximal end of the lead. The atrial electrode may be either a tip electrode or a ring electrode.

The leads of the present invention can be positioned in the patient's heart by using introducer sheaths or stylets, which are well known to those skilled in the art of leads.

Referring back to FIG. 1, shown is a diagrammatic sketch of a pacing system in accordance with this invention. Pacemaker 60 is a standard DDD-type pacemaker, meaning that it has two pulse channels for delivering pacing pulses to the atrium and ventricle respectively. The pacemaker also has sensing channels for sensing and processing spontaneous signals from the atrium (via P waves) and ventricle (via R waves and T waves). The pacemaker may, of course, be a variation of a DDD-type, e.g., a DDD(R), or it can be a 4 chamber pacemaker which also has channels for pacing the left atrium and the left ventricle. As shown, pacemaker 60 is connected to the patient's heart by means of a lead 10. Although FIG. 1 depicts a lead having a brachiocephalic tine, the lead may instead have a three-pronged tine. Essentially, the lead is one of the above-described embodiments of the invention. Atrial electrodes 30 provide delivery of pace pulses to the atrium, and sense spontaneous P waves. The atrial electrodes can be any of the electrodes described above. Ventricular electrodes 18 provide delivery of pace pulses to the ventricle and sense R waves for transmission back to the pacemaker. The ventricular electrodes can be any of the electrodes described above. Of course, a unipolar configuration could also be used in either or both chambers of the heart, in which case only one electrode would be necessary per chamber, the pacemaker being used as the other electrode.

What is claimed is:

1. A pacing lead for pacing a patient's heart, said lead comprising:
   a distal end and a proximal end, and a lead body extending therebetween;
   a ventricular electrode positioned at about said distal end, and a ventricular conductor extending within said lead body from said proximal end to said ventricular electrode; and
   fixation means for substantially fixing a portion of said lead with respect to the junction of the left and right brachiocephalic veins when said distal end is at about the patient's ventricular apex and said lead is positioned to extend proximally from said junction through a portion of the patient's left brachiocephalic vein, wherein said fixation means comprises a short tine element extending from said lead body at an angle substantially corresponding to the angle of said junction.

2. The lead as described in claim 1, wherein the distance from the distal end of the lead to the short tine element is from about 17 cm to about 25 cm.

3. The lead as described in claim 1, further comprising:
   an atrial lead body portion extending from said lead body and having a distal end; and
   an atrial electrode positioned at about said distal end of said atrial lead body portion, and an atrial conductor extending within said atrial lead body portion from said atrial electrode to said proximal end of said lead.

4. The lead as described in claim 3, wherein said electrode is a ring electrode.

5. The lead as described in claim 3, wherein said tine element is positioned from about 7 cm to about 11 cm proximal from the base of said atrial lead body portion.

6. The lead as described in claim 5, wherein said tine element is positioned at about 9 cm proximal from the base of said atrial lead body portion.

7. The lead as described in claim 1, further comprising a ventricular defibrillation coil connected to said ventricular electrode.

8. A pacing lead for pacing a Datient's heart, said lead comprising:
   a distal end and a proximal end, and a lead body extending therebetween;
   a ventricular electrode positioned at about said distal end, and a ventricular conductor extending within said lead body from said proximal end to said ventricular electrode; and
   fixation means for substantially fixing a portion of said lead with respect to the junction of the atrium and the superior vena cava when said distal end is at about the patient's ventricular apex and said lead is positioned to extend proximally from said junction through a portion of the patient's left brachycephalic vein, wherein said fixation means comprises a three-pronged tine.

9. The lead as described in claim 8, wherein the three-pronged tine further comprises an atrial electrode positioned at about said distal end of each of said three prongs, and an atrial conductor extending within each of said three prongs from said atrial electrodes to said proximal end of said lead.

10. The lead as described in claim 8, further comprising a ventricular defibrillation coil connected to said ventricular electrode.

11. A system for pacing a patient's heart, comprising:
    a pacemaker; and
    a lead connectable therewith comprising:
    a distal end and a proximal end, and a lead body extending therebetween;
    a ventricular electrode positioned at about said distal end, and a ventricular conductor extending within said lead body from said proximal end to said ventricular electrode; and
    fixation means for substantially fixing a portion of said lead with respect to the junction of the left and right brachiocephalic veins when said distal end is at about the patient's ventricular apex and said lead is positioned to extend proximally from said junction through a portion of the patient's left brachiocephalic vein, wherein said fixation means comprises a short tine element extending from said lead body at an angle substantially corresponding to the angle of said junction.

12. The system as described in claim 11, wherein the distance from the distal end of the lead to the short tine element is from about 17 cm to about 25 cm.

13. The system as described in claim 12, further comprising:
    an atrial lead body portion extending from said lad body and having a distal end; and
    an atrial electrode positioned at about said distal end of said atrial lead body portion, and an atrial conductor extending within said atrial lead body portion from said atrial electrode to said proximal end of said lead.

14. A system for pacing a patient's heart, comprising:

a pacemaker; and a lead connectable therewith comprising:

a distal end and a proximal ends and a lead body extending therebetween;

a ventricular electrode positioned at about said distal end, and a ventricular conductor extending within said lead body from said proximal end to said ventricular electrode; and fixation means for substantially fixing a portion of said lead with respect to the function of the atrium and the superior vena cava when said distal end is at about the patient's ventricular apex and said lead is positioned to extend proximally from said junction through a portion of the patient's left brachycephalic vein, wherein said fixation means comprises a three-pronged tine.

15. The system as described in claim 14, wherein the three-pronged tine further comprises an atrial electrode positioned at about said distal end of each of said three prongs, and an atrial conductor extending within each of said three prongs from said atrial electrodes to said proximal end of said lead.

* * * * *